United States Patent [19]
Suzuki et al.

[11] Patent Number: 5,451,219
[45] Date of Patent: Sep. 19, 1995

[54] STRETCHABLE ABSORBENT ARTICLE

[75] Inventors: Migaku Suzuki, Kanagawa; Hiroaki Fukui, Saitama, both of Japan

[73] Assignee: Paragon Trade Brands, Inc., Federal Way, Wash.

[21] Appl. No.: 98,603

[22] Filed: Jul. 28, 1993

[51] Int. Cl.⁶ .................. A61F 13/15; A61F 13/20
[52] U.S. Cl. .................... 604/385.2; 604/358; 604/367; 604/369; 604/373
[58] Field of Search ............... 604/358, 367-369, 604/373, 378, 385.1, 385.2; 428/230, 233, 236

[56] References Cited

U.S. PATENT DOCUMENTS

| | | | |
|---|---|---|---|
| 2,273,542 | 2/1942 | Tasker | 604/385.2 |
| 3,575,782 | 4/1971 | Hansen . | |
| 4,515,595 | 5/1985 | Kievit et al. . | |
| 4,525,407 | 6/1985 | Ness . | |
| 4,552,795 | 11/1985 | Hansen et al. . | |
| 4,639,949 | 2/1987 | Ales et al. . | |
| 4,640,859 | 2/1987 | Hansen et al. . | |
| 4,655,760 | 4/1987 | Morman et al. | 604/385.2 |
| 4,710,189 | 12/1987 | Lash . | |
| 4,834,741 | 5/1989 | Sabee . | |
| 4,840,692 | 6/1989 | Kamstrup-Larsen | 604/368 |
| 4,847,134 | 7/1989 | Fahrenkrug et al. . | |
| 4,891,258 | 1/1990 | Fahrenkrug . | |
| 4,892,535 | 1/1990 | Bjornberg et al. . | |
| 4,908,247 | 3/1990 | Baird et al. . | |
| 4,977,011 | 12/1990 | Smith . | |
| 4,978,570 | 12/1990 | Heyn et al. | 604/369 |
| 4,984,584 | 1/1991 | Hansen et al. . | |
| 5,151,091 | 9/1992 | Glaug et al. | 604/378 |
| 5,366,452 | 11/1994 | Widlund et al. | 604/358 |

FOREIGN PATENT DOCUMENTS

| | | |
|---|---|---|
| 563841 | 3/1983 | Australia . |
| 0027303 | 4/1981 | European Pat. Off. . |
| 0211197 | 2/1987 | European Pat. Off. . |
| WO80/00676 | 4/1980 | WIPO . |
| WO91/11161 | 8/1991 | WIPO . |
| WO91/15355 | 10/1991 | WIPO . |

*Primary Examiner*—Randall L. Green
*Assistant Examiner*—P. Zuttarelli
*Attorney, Agent, or Firm*—Dressler, Goldsmith, Shore & Milnamow, Ltd.

[57] ABSTRACT

A stretchable absorbent article, such as a diaper, a sanitary product or other absorbent member, comprises a liquid permeable layer, and a liquid impermeable elastic layer stretchably secured to the liquid permeable layer at discrete regions so as to form regions of nonsecurement between the discrete regions of securement. The liquid permeable layer forms corrugations at respective regions of nonsecurement for respectively defining channels between the liquid permeable layer and the liquid impermeable elastic layer. Absorbent material is disposed in selected ones of the channels.

26 Claims, 7 Drawing Sheets

STRETCHABLE ABSORBENT ARTICLE

TECHNICAL FIELD

The present invention generally relates to absorbent articles such as diapers, sanitary products, and absorbent members suitable for use in such diapers, and more particularly to an elastically stretchable absorbent article.

BACKGROUND OF THE INVENTION

Disposable absorbent articles, such as diapers, sanitary products, incontinent pads, and the like have obtained wide acceptance by consumers. Such absorbent articles generally include a liquid permeable sheet, a liquid impermeable sheet for preventing body exudates from leaking out, and an absorbent member interposed therebetween for absorbing such body exudates.

Conventional liquid impermeable sheets provide satisfactory liquid impermeablility. However, those sheets are not flexible enough to closely conform to the shape of wearer's body, and consequently provide poor leakage protection.

Various types of materials have been proposed for use in absorbent members and may have been put into actual practice. Furthermore, with progress of development work on superabsorbent material comprising polymeric material capable of absorbing more than ten times its weight of liquids, absorbent members incorporating such superabsorbent material have been widely utilized.

The absorbent members as have been already proposed or put into actual practice have a panel configuration for presenting a flat absorbent surface to be contacted by liquids over its entire area in an effort to obtain target liquid absorbency. Although such absorbent members provide satisfactory liquid absorbency, they are not flexible enough to conform to a wearer's body during their use. In particular, absorbent members incorporating superabsorbent material exhibit substantial increase in rigidity when the superabsorbent material absorbs liquids. This increase in rigidity of the absorbent members causes poor conformity thereof to the wearer's body, which leads to liquid leakage from the sides thereof.

The present invention provides a highly-functional absorbent article which is capable of absorbing a desirable amount of liquids, and is at the same time elastically stretchable and contractible to better conform to the wearer's body during use.

SUMMARY OF THE INVENTION

The present invention provides a stretchable absorbent article for fitting about and enclosing a waist portion of a wearer. The article comprises a main body comprising an elastic composite sheet. The elastic composite sheet comprises an elastic sheet and a non-woven material in the form of non-woven fabric secured to at least one surface of the elastic sheet. The non-woven fabric is secured to the elastic sheet continuously in a first direction and intermittently in a second direction perpendicular to the first direction to define therebetween a plurality of parallel channels extending in the first direction.

The elastic composite sheet may be dual-layered (i.e., doubled) in the region of at least one of a front waist portion, a rear waist portion, a crotch region, and a leg-hole surrounding portion in the main body.

The present invention further provides a stretchable absorbent article which comprises a liquid permeable layer, and a liquid impermeable elastic layer stretchably secured to the liquid permeable layer by a plurality of laterally spaced, parallel lines of securement so as to form laterally spaced, parallel regions of nonsecurement. The liquid permeable layer forms corrugations at the respective regions of nonsecurement for defining a plurality of parallel channels between the liquid permeable layer and the liquid impermeable elstic layer. Absorbent material is disposed in a selected location of the absorbent article.

In another aspect of the present invention, there is provided a stretchable absorbent member which comprises a liquid permeable layer, and a liquid impermeable elastic layer stretchably secured to the liquid permeable layer at discrete regions so as to form regions of nonsecurement between the discrete regions of securement. The liquid permeable layer forms corrugations at the respective regions of nonsecurement for defining respective channels between the liquid permeable layer and the liquid impermeable elastic layer. Absorbent material is disposed in selected ones of the channels.

The present invention further provides a stretchable absorbent member which comprises a liquid permeable layer, and a liquid impermeable elastic layer stretchably secured to the liquid permeable layer by a plurality of laterally spaced, parallel lines of securement so as to form laterally spaced, parallel regions of nonsecurement. The liquid permeable layer forms corrugations at the respective regions of nonsecurement for defining a plurality of parallel channels between the liquid permeable layer and the liquid impermeable elastic layer. Absorbent material is disposed in selected ones of the plurality of channels.

Other features and advantages of the present invention will become readily apparent from the following detailed description, the accompanying drawings, and the appended claims.

DETAILED DESCRIPTION

While the present invention is susceptible of embodiment in various forms, there is shown in the drawings and will hereinafter be described in detail specific embodiments thereof, with the understanding that the present disclosure is to be considered as an exemplification of the invention, and is not intended to limit the invention to the specific embodiments illustrated.

Figure 1:
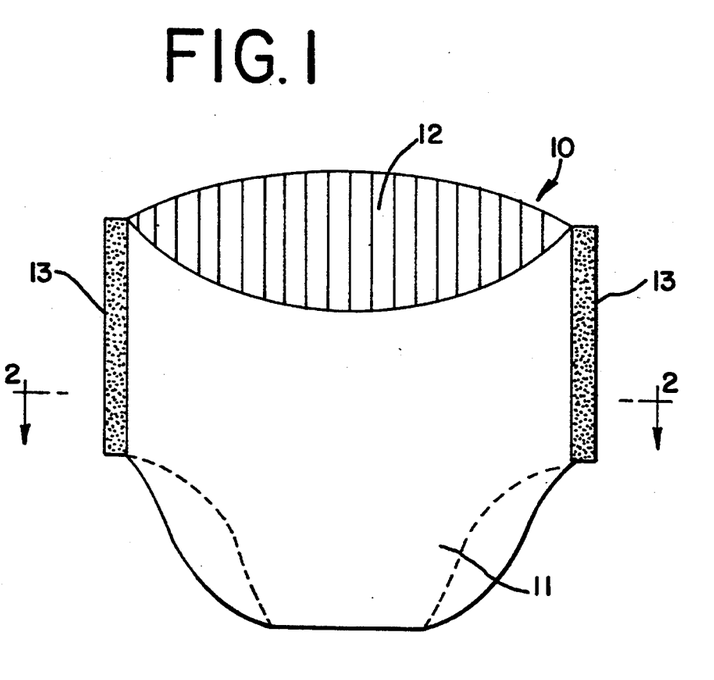
FIG. 1 is a perspective view illustrating a first embodiment of a liquid impermeable protective article in accordance with the present invention.
Figure 2:
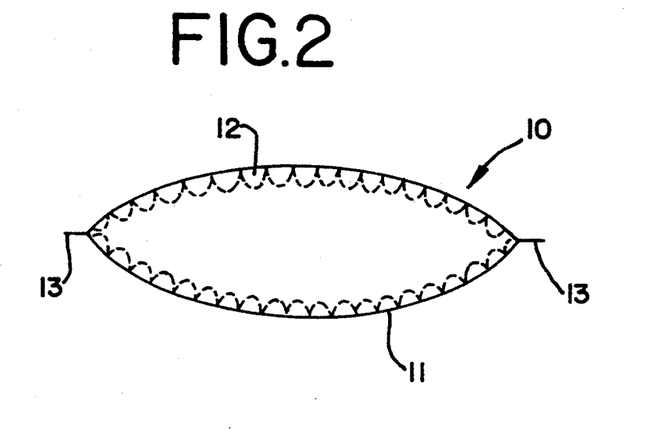
FIG. 2 is a cross-sectional view taken along a line A—A of FIG. 1.

Referring now to the drawings, FIG. 1 is a perspective view illustrating an absorbent article, such as a liquid impermeable protective article of a pant type, embodying the principles of the present invention. FIG. 2 is a cross-sectional view taken along the line A—A of FIG. 1. In FIGS. 1 and 2, the liquid impermeable protective article is provided with a main body 10 which comprises a first portion 11 having a configuration covering a front face of a body waist and a second portion 12 for covering a back face of the body waist. These first and second portions 11, 12 are formed by cutting a composite sheet 1, as will be hereinafter described, into a generally-rectangular piece, bi-folding the piece along a longitudinal center portion and joining the folded portions to each other at joint portions 13 located at respective lateral ends of the folded portions.

Figure 3:
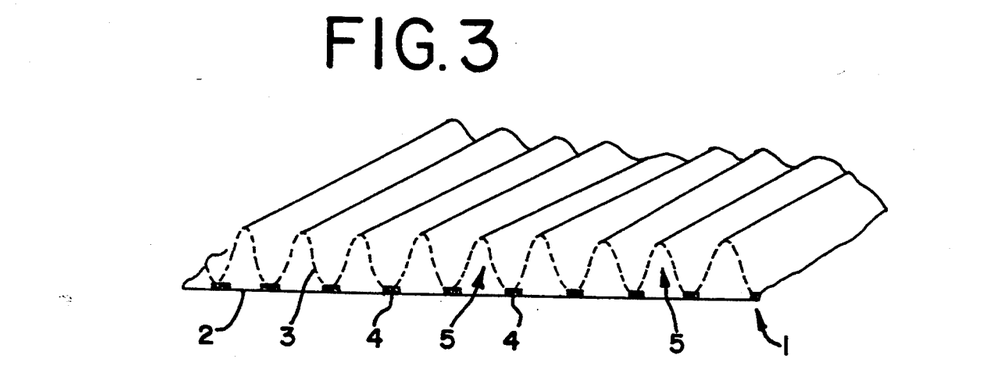
FIG. 3 is a fragmentary perspective view of a composite sheet of the protective article of FIG. 1.

The composite sheet 1 constituting the first and second portions 11, 12 is constructed by securing a non-woven fabric 3 onto at least one surface of a liquid impermeable elastic sheet 2, as shown in FIG. 3. The non-woven fabric 3 is secured to the elastic sheet 2 continuously in a first direction and intermittently in a second direction transverse to the first direction. The securement of these two elements are made along parallel securement lines 4 spaced from each other such as at regular intervals. A width of the non-woven fabric 3 is formed to be greater than that of the elastic sheet 2 between adjacent securement lines 4, so that a plurality of parallel channels 5 extending in the first direction are formed between the elastic sheet 2 and the non-woven fabric 3. This composite sheet 1 is cut or contoured in accordance with desired shapes and dimensions of the first and second portions 11, 12 which are then joined to each other so as to form the non-woven fabric 3 to face inwardly.

In a liquid impermeable protective article 10 of such construction, the inwardly placed non-woven fabric 3 contacts the body of a wearer when the article 10 is applied to the wearer and a plurality of elongated channels 5 are provided between such non-woven fabric 3 and the elastic sheet 2. Accordingly, breathability and flexibility of the non-woven fabric 3 per se and the channels 5 provides a comfortable feeling during use, by softness to skin. The outwardly placed elastic sheet 2 is liquid impermeable, so that liquids are effectively prevented from leaking through the article.

Figure 4:
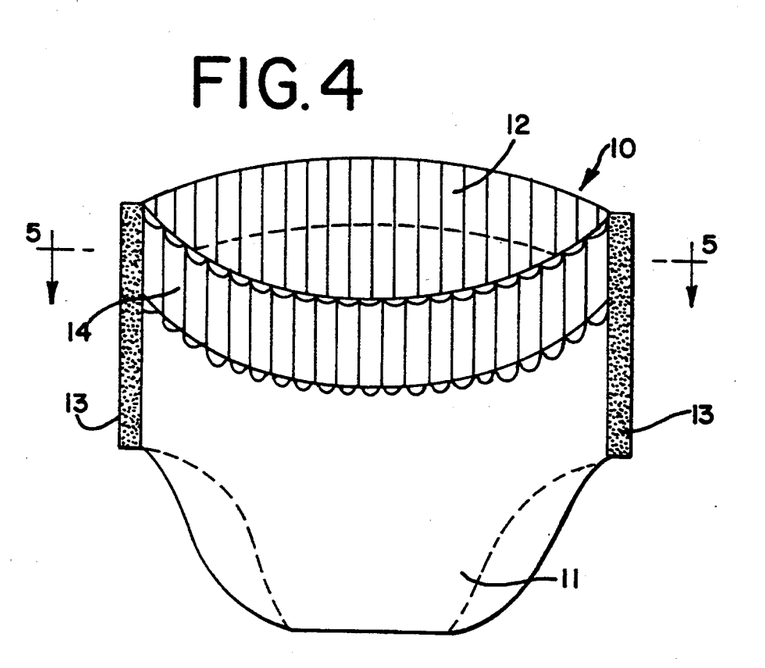
FIG. 4 is a perspective view of a second embodiment of a liquid impermeable protective article in accordance with the present invention.
Figure 5:
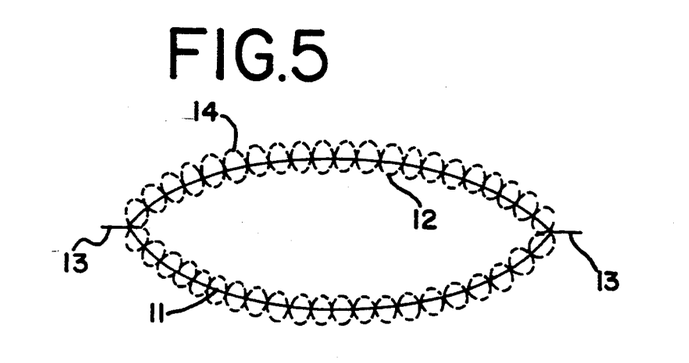
FIG. 5 is a cross-sectional view taken along a line B—B of FIG. 4.

Although the main body 10 comprising the first and second portions 11, 12 is illustrated as being single-layered in its entire region in the embodiment of FIG. 1, it may be dual-layered (i.e., doubled) by placing a belt-like strengthening member 14 of a suitable width cut from the composite sheet 1 onto respective upper end portions of the first and second portions 11, 12, as illustrated in FIGS. 4 and 5. This construction increases strength as well as elastic contractibility in such portions, so that any breakage which may be caused by a careless handling of the article during use will be avoided. Its stability about the body waist during application will also be improved. The securement of the main body 10 and the strengthening member 14 may be readily made by the use of heat compression, adhesives of the hotmelt type and the like. Such strengthening may alternatively be accomplished by forming the main body 10 longer than a desired dimension and folding its upper end portion onto itself.

Figure 6:
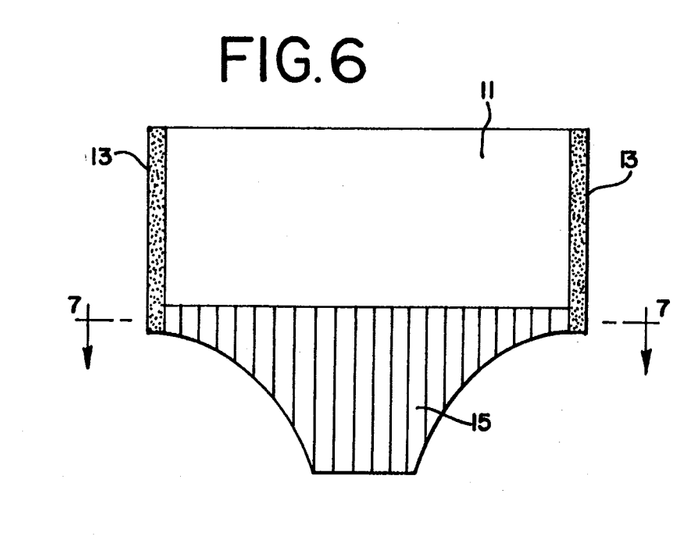
FIG. 6 is a front view of a third embodiment of a liquid impermeable protective article in accordance with the present invention.
Figure 7:
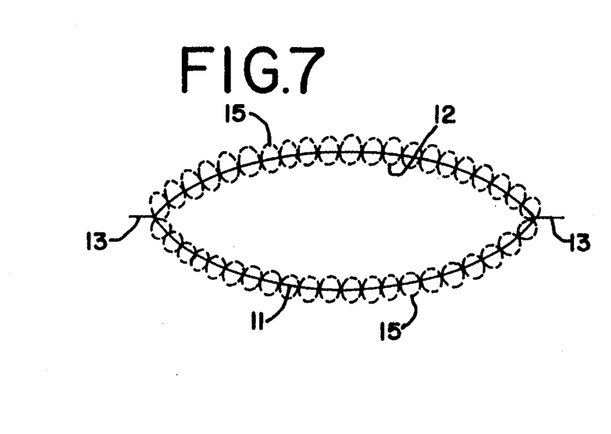
FIG. 7 is a cross-sectional view taken along a line C—C of FIG. 6.
Figure 8:
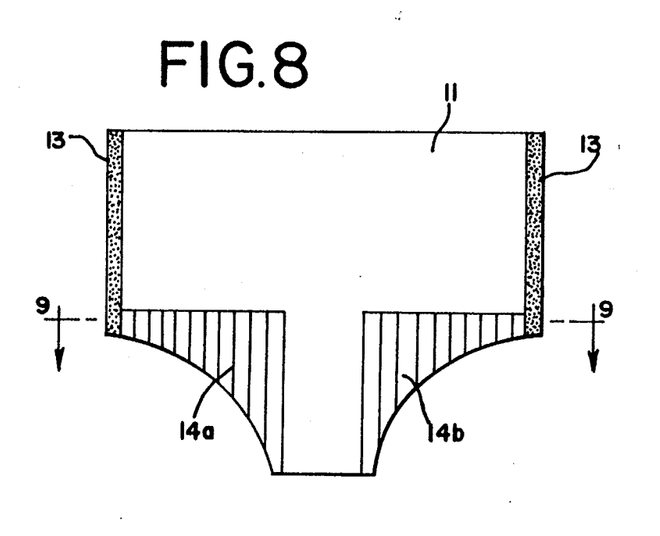
FIG. 8 is a front view of a fourth embodiment of a liquid impermeable protective article of the present invention.
Figure 9:
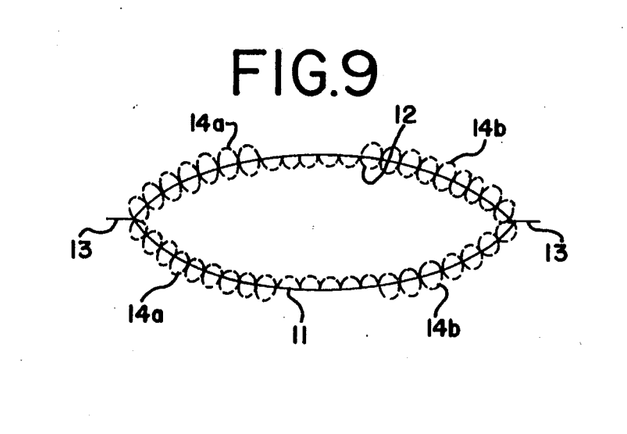
FIG. 9 is a cross-sectional view taken along a line D—D of FIG. 8.

Alternatively, the main body 10 may be dual-layered in its crotch region by providing a strengthening member 15 having a shape corresponding to such region, as illustrated in FIGS. 6 and 7. In still another embodiment, reinforcing members 14a, 14b may be respectively attached to two portions surrounding the leg holes, as illustrated in FIGS. 8 and 9. In either embodiment, the leg hole portions, to which a relatively great stretching force is applied when the article is put on or removed from the wearer, are constructed to be dual-layered, so that breakage in such portions is effectively prevented. The crotch or leg hole strengthening portion may be combined with a waist strengthening portion as illustrated in FIG. 4.

Figure 10:
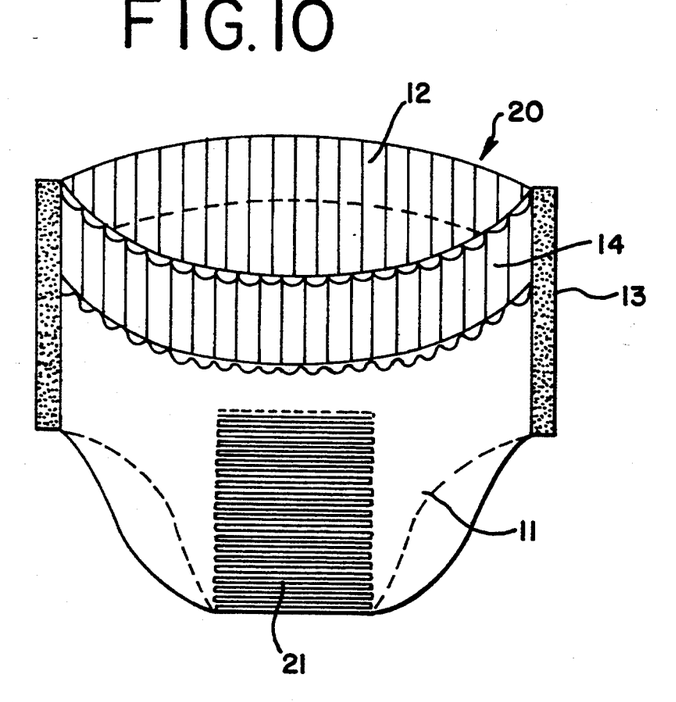
FIG. 10 is a cross-sectional view of a fifth embodiment of a liquid impermeable protective article of the present invention.

FIG. 10 shows another embodiment of a liquid impermeable protective article in accordance with the present invention. The liquid impermeable protective article 20 of this embodiment has the main body 10 of the construction, in which the first portion 11 and the second portion 12 are joined to each other at joint portions 13, formed with the folded portion 14 in its upper end portion, similar to the construction shown in FIG. 4. The article 20 is also provided with an absorbent body 21 positioned in its crotch region. The absorbent body 21 may be of the type as employed for conventional diapers or sanitary napkins and fixedly secured in a predetermined position by means such as glues, hotmelt adhesives and the like.

Such an absorbent body as described above is per se rigid, and accordingly lacks elasticity and flexibility like the composite sheet 1 has, with the result that elasticity in a portion of the main body 10 is disturbed when such a rigid absorbent body is attached to the portion of the main body of the present article. The attachment as illustrated in FIGS. 11 and 12 may be preferably utilized in order to avoid such drawbacks.

Figure 11:
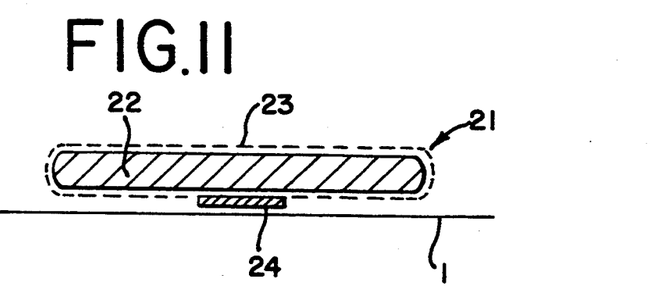
FIG. 11 is a cross-sectional view illustrating an absorbent body and attachment means thereof in the liquid impermeable protective article of FIG. 10.

The absorbent body 21, as illustrated in FIG. 11, comprises an absorbent member 22 and a liquid permeable cover 23 for enclosing the absorbent member 22. The absorbent body 21 is at its transverse center portion secured to the non-woven fabric side of the composite sheet 1 only along a band-like elongated securement portion 24 extending a full length of the absorbent body, and formed such as by adhesives, hotmelts and the like. Such construction permits the composite sheet to be less affected by the securement of the absorbent body 21 thereto and allows the absorbent body 21 to be freed from the stretching and contracting action of the composite sheet. Accordingly, the construction permits any deformation of the absorbent body along a wearer's body shape and accomodates a dimensional change of the absorbent member after liquid absorption. Furthermore, the absorbent body does not move or deviate from the predetermined position. Therefore, leakage is completely prevented and a very comfortable feeling is achieved.

Figure 12:
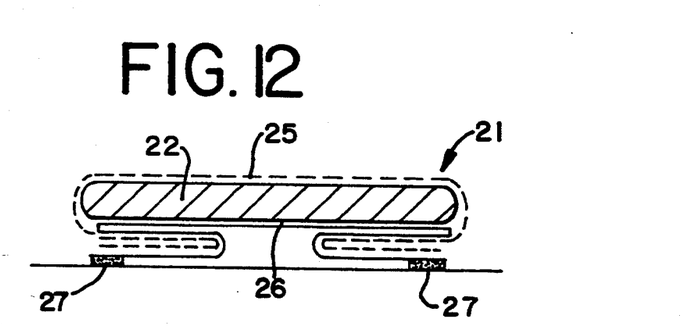
FIG. 12 is a cross-sectional view illustrating another embodiment of an absorbent body and attachment means thereof in the liquid impermeable protective article of FIG. 10.

Alternatively, the absorbent body 21 may comprise a liquid permeable topsheet 25 for covering top and side surfaces of the absorbent member 22 and a backsheet 26 for covering a bottom surface of the absorbent member 22, as illustrated in FIG. 12. Portions of the topsheet 25 and the backsheet 26 extending from each side edge of the absorbent member 22 are folded beneath the absorbent member 22 to take a U-shaped configuration. The portions are secured to the composite sheet 1 at band-like securement portions 27 which are located at leading ends of the extension portions, and are formed such as by adhesives, hotmelts and the like. In this construction, the absorbent member 22 takes a position as if it "floats" above the composite sheet so that movement of the absorbent member 22 becomes substantially independent of movement of the composite sheet. This provides about the same or higher degrees of leakage protection and comfort than the construction of FIG. 10.

Figures 13, 14, 15, 16:
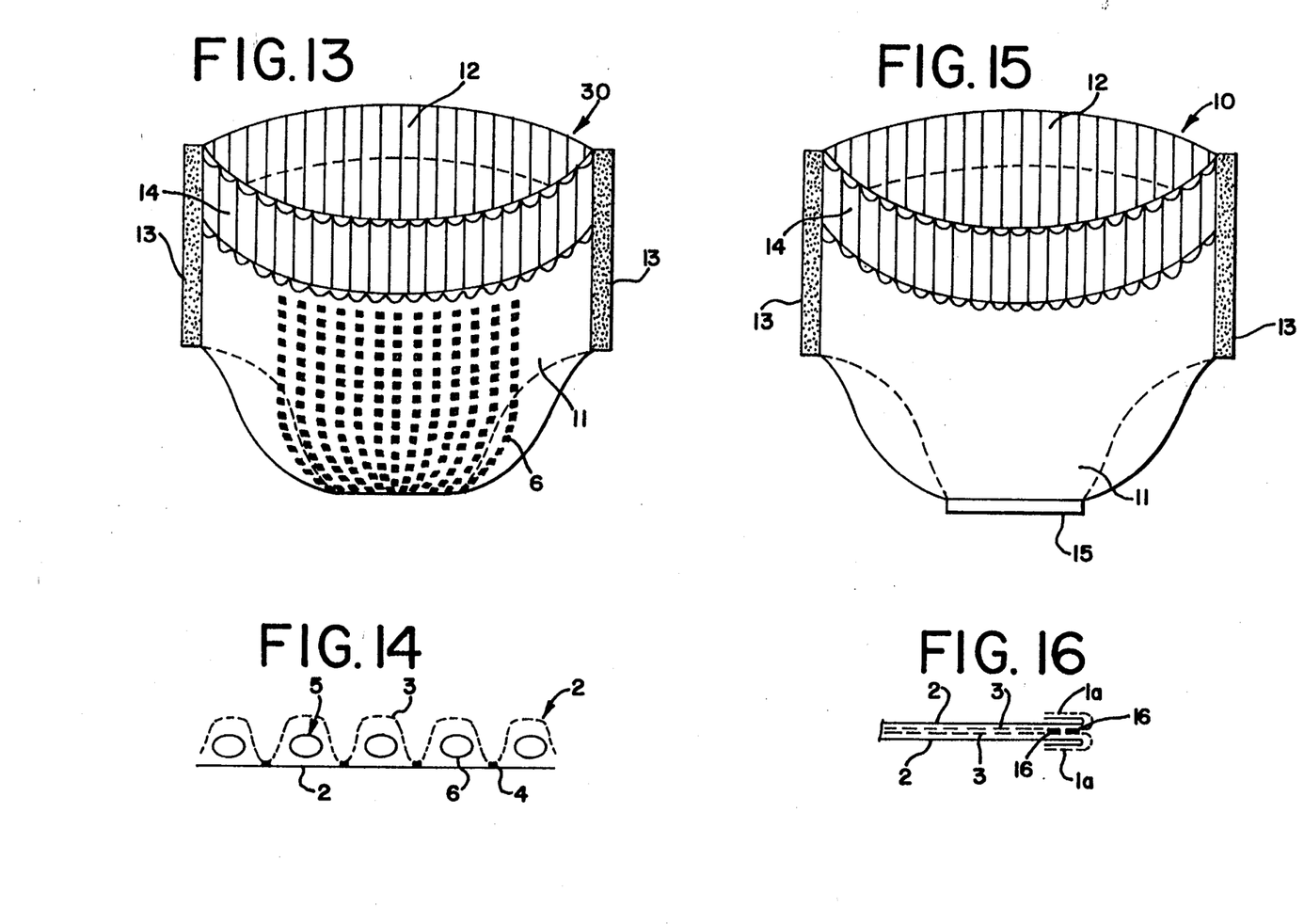
FIG. 13 is a cross-sectional view illustrating a sixth embodiment of a liquid impermeable protective article in accordance with the present invention.
FIG. 14 is a fragmentary enlarged cross-sectional view of FIG. 13.
FIG. 15 is a perspective view illustrating a seventh embodiment of a liquid impermeable protective article in accordance with the present invention.
FIG. 16 is a cross-sectional view illustrating a preferred construction of a securement portion of a liquid impermeable protective article in accordance with the present invention.

FIG. 13 shows another embodiment of the liquid impermeable protective article 30 which is intended to further enhance the effects of the present invention. In this embodiment, the composite sheet 1 includes absorbent material 6 positioned within channels defined between the elastic sheet 2 and the non-woven fabric 3, as illustrated in FIG. 14. The absorbent material 6 may be positioned in the entire region of the composite sheet 1. Alternatively, the absorbent material 6 may be positioned only in a crotch region of the composite sheet 1 with which contact with body exudate is possible, as illustrated in FIG. 13. Such absorbent material 6 absorbs body exudates which have passed through the non-woven fabric 3 and entered into channels 5. This eliminates the need to provide a separate absorbent body.

Suitable absorbent material 6 for placement within the channels 5 includes hydrophilic material such as wood pulp or cotton, or synthetic fibrous material such as polypropylene, polyester and the like which is hydrophilized by hydrophilic treatment. Preferably, such absorbent material utilizes superabsorbent material which is generally referred to as S.A.P. (Super Absorbent Polymer) capable of absorbing several times its own weight of water or aqueous liquids.

In the event the superabsorbent material is utilized in a particulate form, the non-woven fabric constituting walls of the channels 5 is required to be of high quality in terms of a filtering function to prevent the particulates from passing therethrough. Preferably, the superabsorbent material may be incorporated in the absorbent material in various forms. One example would be strips of suitable widths cut from a composite sheet material comprising superabsorbent material particles and wood pulp or a fibrous web. Another example is a bundle of fibrous superabsorbent material, such as RUNSEAL manufactured and marketed by Toyobo Corp. under such trade name. Strips slit from a fibrous web with superabsorbent material deposited on its surface may also be employed. Such material may be manufactured by polymerizing and cross-linking a monomer solution placed on the fibrous web surface.

The volume of the absorbent material increases as it absorbs liquids. In particular, the superabsorbent material exhibits a drastic volume change before and after liquid absorption. Therefore, when a cross-sectional area of the absorbent material is selected to substantially correspond to that of the channel space, the channel would be enlarged by the amount that the superabsorbent material swells as it absorbs liquids. Such enlargement would be readily accommodated primarily by a stretching action of the elastic sheet. However, it is preferable that such a cross-sectional area of the absorbent material is selected within a range such that the cross-sectional area after swelling remains smaller than that of the channel space when the swelling of the absorbent material is drastic, such as with superabsorbent material, or such a volume change is not desirable. Such range selection creates a free space within the channel, so that superabsorbent material is able to swell freely without restriction and fully utilize its absorbent capacity.

In respective embodiments as illustrated in FIGS. 1–14, the main body is constructed by forming leg holes on a generally-rectangular single composite sheet 1, bi-folding the sheet 1 along its longitudinal center portion and joining or securing the folded portions to each other at their respective opposite side ends. In an alternative embodiment as shown in FIGURE 15, the main body 10 is constructed by securing the first and second portions 11, 12 separately cut from the composite sheet along side end securement portions 13 and a lower end securement portion 15.

In respective embodiments as described above, the securement portions for securing the first and second portions to each other may be formed by securing opposing inwardly-facing non-woven fabrics 3 to each other by suitable securement means such as heat-sealing, adhesives of the hotmelt type and the like. Preferably, the main body 10 is, at portions corresponding to the securement portions, folded outwardly to define folded portions 1a having a suitable width, preferably equal to that of the securement portion. The folded portions 1a are secured together along securement lines 16. In this construction, the U-folded non-woven fabrics 3 are positioned at side edges of respective securement portions so that those portions provide soft and smooth surfaces such as against an outside clothing thereby providing a more comfortable feeling during wearing as contrasted to the previous construction wherein cut edges of the elastic sheet 2 project to those portions.

Figure 17:
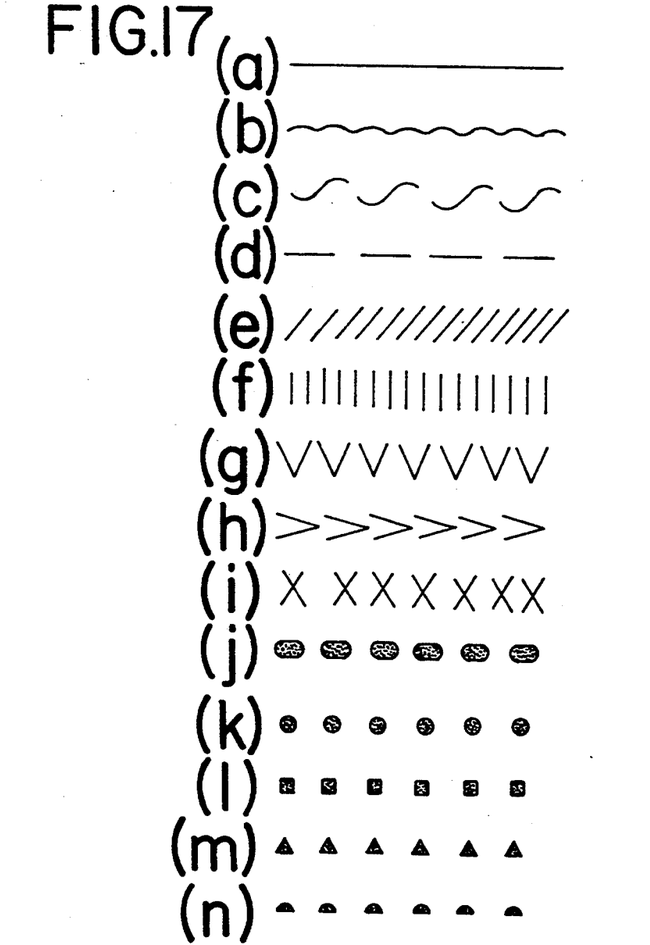
FIG. 17 is an explanatory view illustrating various securement patterns applied to a securement portion of a liquid impermeable protective article in accordance with the present invention.

In addition, the securement of the composite sheet 1 to itself at securement portions 13, 15 may be made along two securement lines 16 parallel to each other, as illustrated in FIG. 16. Alternatively, the securement may be made in such patterns (a)–(n) as illustrated in FIG. 17. Particularly, intermittent patterns such as (c)–(n) in FIG. 17 provide lower strength than continuous patterns. Such intermittent patterns may be preferably utilized for articles such as diaper covers which are desired to be removed from a wearer by breaking the main body 10.

It has been found that the very flexible nature of the composite sheet allows folding thereof into a compact form so that carrying and use thereof are facilitated.

Figure 18:
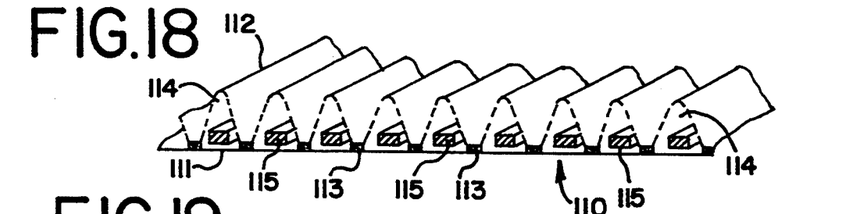
FIG. 18 is a fragmentary perspective view illustrating one embodiment of the absorbent member embodying the principles of the present invention.
Figure 19:
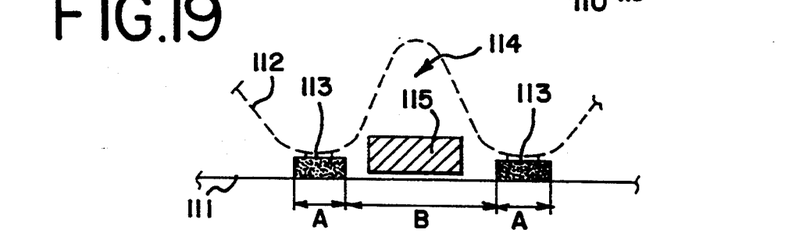
FIG. 19 is a fragmentary enlarged cross-sectional view of the absorbent member of FIG. 18.

FIG. 18 is a perspective view illustrating an absorbent member embodying the principles of the present invention. FIG. 19 is a fragmentary enlarged cross-sectional view of FIG. 18. In FIGS. 18 and 19, an absorbent member 110 in a sheet form comprises an elastic sheet 111 and a non-woven fabric 112 which are secured together continuously in a first direction of the non-woven fabric 112, such as in a machine direction, and intermittently in a second direction perpendicular to the first direction, i.e. in a cross-machine direction, along securement lines 113. A width of the non-woven fabric 112 between neighboring securement lines 113 is selected to be greater than that of the elastic sheet 111 so that a plurality of channels 114 extending in the machine direction are formed between the elastic sheet 111 and the non-woven fabric 112.

An absorbent material 115, such as of an elongated band-like configuration cut from superabsorbent sheet is positioned in the channels 114 so as to extend a full length of the respective channel 114. A cross-sectional area of the absorbent material 115 is selected to be about ½ or smaller, for example 1/5 of that of the channel 114.

The absorbent member 110 thus constructed is placed in actual use so that the non-woven fabric 112 contacts liquids. For example, when the absorbent member 110 is incorporated in a diaper or sanitary napkin, the non-woven fabric 112 serves as a topsheet for facing the body of the wearer and the elastic sheet 111 serves as a liquid impermeable backsheet for preventing liquid leakage. The liquid is absorbed by the absorbent materials 115 positioned in the channels 114.

Figure 20:
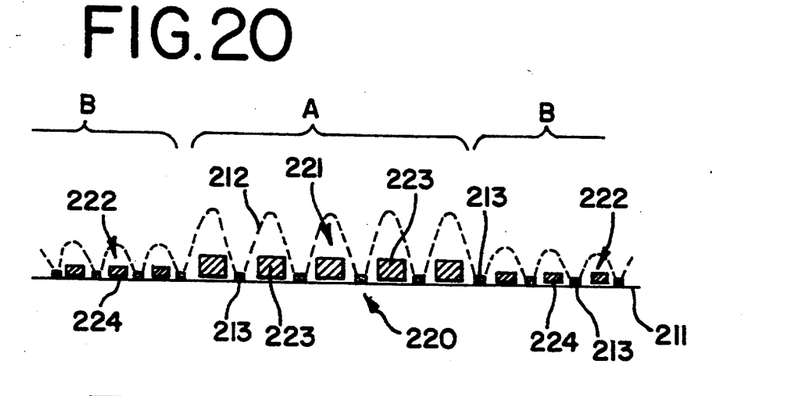
FIG. 20 is a cross-sectional view illustrating another embodiment of the absorbent member in accordance with the present invention.
Figure 21:
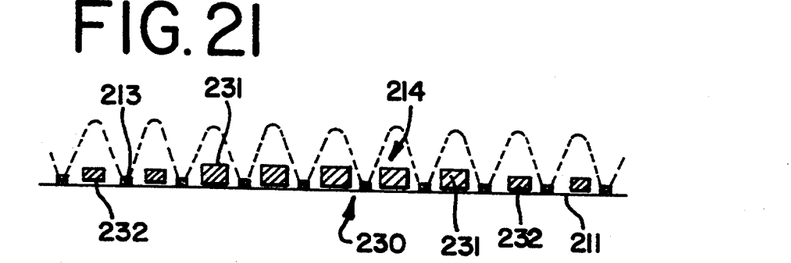
FIG. 21 is a cross-sectional view illustrating still another embodiment of the absorbent member in accordance with the present invention.

FIG. 20 illustrates another embodiment of the absorbent member in accordance with the present invention. The absorbent member 220 in this embodiment has two different channels 221, 222 of different cross-sectional areas. A cross-sectional area of each of the first channels 221, which are positioned in a laterally central portion A of the absorbent sheet 220, is greater than that of the second channels 222 which are positioned in lateral side portions B on opposite sides of the laterally central portion A. A cross-sectional area of first absorbent materials 223 placed in the first channels 221 is proportionally greater than that of second absorbent materials 224 placed in the second channels 222.

The absorbent member 220 of the construction as illustrated in FIG. 20, accordingly has a higher liquid absorbency in the central portion A than in the side portions B. This feature is especially suitable for use in articles having a narrow central region to which liquids are discharged in a concentrated manner.

The channel structure of the absorbent members as illustrated in FIGS. 18–21 is in its dry state (before liquid absorption) effective in enhancing diffusion and flow-in of liquids and air in a longitudinal direction, and in its wet state (after liquid absorption) effective in enhancing liquid diffusion to rapidly diffuse liquids received therein in the longitudinal direction, with the result that liquids are distributed within entire regions of the absorbent members placed in the channels in a short period of time, and effective absorbency of the absorbent sheet is exhibited.

Means for securing the elastic sheet 211 and the non-woven fabric 212 so as to form channels 214 are not limited to any specific manner. For example, the pre-shaped wavy non-woven fabric 212 may be placed on the flat elastic sheet 211 so as to contact to each other. The contact portions are then secured together by any suitable means such as adhesives, sonic-sealing, heat-compression and the like. The most preferable method is to finish securement by placing the non-woven fabric in contact with the elastic sheet while it is tacky in its manufacturing process.

Alternative means for forming channels may utilize a difference between machine-directional and cross machine-directional elongation rates of the non-woven fabric. Specifically, the non-woven fabric is placed on at least one surface of the elastic sheet. They are secured together continuously in the machine direction and intermittently in the cross-machine direction to form the composite sheet. The composite sheet is then stretched in a cross-machine direction at a ratio exceeding an elastic limit of the non-woven fabric so that a permanent elongation is created in the non-woven fabric. When released, the channels are formed in the composite sheet since the permanently elongated non-woven fabric has a width greater than a width of the elastic sheet between the neighboring securement lines. Non-woven fabrics having a higher elongation rate in the cross-machine direction than in the machine direction such as illustrated as No. 3 and No. 4 in Table I are suitably used for such method for forming channels.

Figure 22:
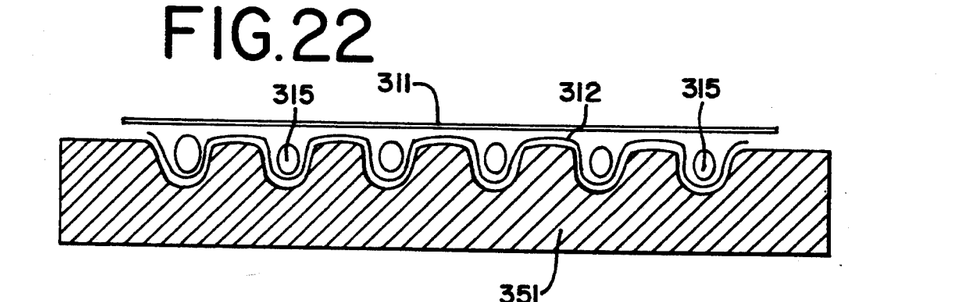
FIG. 22 is a cross-sectional view illustrating one mold embodiment which is employed to manufacture the absorbent member in accordance with the present invention.
Figure 23:
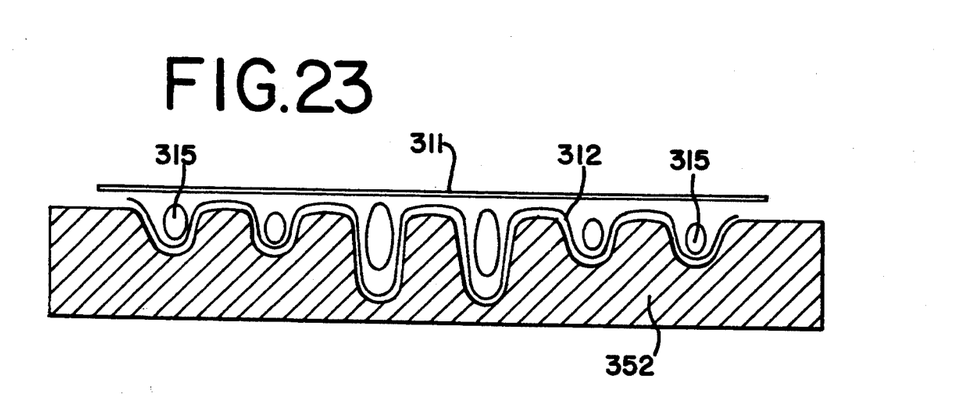
FIG. 23 is a cross-sectional view illustrating another mold embodiment which is employed to manufacture the absorbent member in accordance with the present invention.

The placement of the absorbent material in channel structures may be performed by positioning the absorbent material between the elastic sheet and the non-woven fabric before they are secured together to form channels. However, in order to place the absorbent material in precise positions in actual industrial practice, a method as illustrated in FIGS. 22 and 23 may be preferably employed. The non-woven fabric 312 is tucked into a mold 351 or 352 having rows of grooves, mechanically or by vacuum suction so that a plurality of spaced top surface portions and channels between the adjacent top surface portions are provided. A plurality of individual absorbent materials 315 are then placed in the respective channels of the non-woven sheet 312. Finally, the elastic sheet 311 is secured onto the spaced top surface portions of the non-woven fabric 312 to enclose the individual absorbent materials 315 within the respective channels. The mold 351 illustrated in FIG. 22 has a plurality of grooves of equal cross-sectional area into which the individual absorbent materials of equal cross-sectional area are positioned. On the other hand, the mold 352 illustrated in FIG. 23 has central grooves having a greater cross-sectional area than that of side grooves on opposite sides of the central grooves. Likewise, the individual absorbent materials 315 positioned in the central grooves have a greater cross-sectional area than that in the side grooves.

Additionally, the composite absorbent member in accordance with the present invention has a construction such that absorbent materials of high liquid absorbency are positioned in the channels defined between the elstic sheet and the non-woven fabric. Liquids pass through the non-woven fabric into the channels where they are absorbed by the absorbent materials.

Suitable absorbent materials for placement within the channels include hydrophilic material such as wood pulp or cotton, or synthetic fibrous material such as polypropylene, polyester and the like which are hydrophilized by hydrophilic treatment. Preferably, such absorbent materials utilize superabsorbent material which is generally referred to as S.A.P. (Super Absorbent Polymer) capable of absorbing up to several tens times its own weight of water or aqueous liquids.

In the event the superabsorbent material is utilized in a particulate form, the non-woven fabric constituting walls of the channels is required to be of high quality in terms of filter function to prevent the particles from passing therethrough. Preferably, the superabsorbent material may be incorporated in the channels in various forms. One example would be strips of suitable widths cut from a composite sheet material comprising superabsorbent material particles and wood pulp or fibrous web. Another example is a bundle of fibrous superabsorbent material, such as RUNSEAL manufactured and marketed by Toyobo Corp. under such trade name. Strips slit from a fibrous web with superabsorbent material deposited on its surface may also be employed. Such material may be manufactured by polymerizing and cross-linking a monomer placed on the fibrous web surface.

The volume of the absorbent material increases as it absorbs liquids, In particular, the superabsorbent material exibits a drastic volume change before and after liquid absorption. Therefore, when a cross-sectional area of the absorbent material is selected to be substantially correspond to that of channel space, the channel would be enlarged by the amount that the superabsorbent material swells as it absorbs liquids. Such enlargement would be readily accomodated primarily by a stretching action of the elastic sheet. However, it is preferable that such a cross-sectional area of the absorbent material is selected within a range such that the cross-sectional area after swelling stays smaller than that of the channel space when swelling of the absorbent material is drastic such as of superabsorbent material, or such a volume change is not desirable. Such range selection creates a free space within the channel, so that superabsorbent material is able to swell freely without restriction and fully utilize its absorbent capacity.

When it is desired that a selected portion of the absorbent surface of the absorbent member of the present invention absorb higher volume of liquids than the remaining portions of the absorbent surface, the amount of the absorbent materials positioned in the channels located in the selected portion may be increased. Such density distribution of the absorbent members may preferably be made by varying cross-sectional areas of the channels for enclosing absorbent meterials in selected portions of the absorbent surface in accordance with a desired distribution. The absorbent member of such construction is particularly suitable for use in infant diapers and sanitary napkins which have a central target zone into which liquids are heavily discharged.

The elastic sheet for use in the absorbent member of the present invention includes thin-layered sheet such as films consisting of a material selected from a natural or synthetic rubber, polyurethane, styrene-butadien block polymer, EVA, LLDPE of ultra low density ethylene-propylene elastomer, ethylene-methylacrylate elastomer and a mixture thereof with a styrene-ethylene-butadien-styrene block copolymer; co-extruded films of polyurethane elastomers and polyolefine elastomers; and polyurethane meltblown non-woven fabrics.

The non-woven fabric for use in the absorbent member of the present invention is selected by considering firstly its function as an absorbent and secondly its ability to form channels.

In order for the non-woven fabric to function as an absorbent, it needs to be liquid permeable without adverse result during use against skin. Its adhesive characteristic with film, and its ability to maintain a channel configuration, should be taken into consideration from a view point of the ability to form channels.

Based on the above considerations, the following non-woven fabrics may be advantageously employed; non-woven fabrics of a lower basis weight (preferably lower than 50 g/m$^2$) manufactured by methods such as dry-laid, spunbond, spunlace and the like, from fibers of relatively low denier ( preferably lower than 5 d ) comprising hydrophobic synthetic fibers such as polypropylene, polyester, nylon and the like, hydrophilic fibers such as rayon, cotton and the like, or any combination thereof.

Non-woven fabrics predominantly comprising hydrophobic fibers may be preferably treated by surfactants which are safe to skin to render the fabrics highly liquid permeable. When the non-woven fabric predominantly comprises hydrophilic fibers such as rayon fibers, it is desirable that such hydrophilic fibers comprise anti-bacterial fibers that are safe to the skin for the purpose of preventing adverse effects to skin which may be caused by high water content in a surface layer of the hydrophilic fibers. Such commercially available fibers as CHITOCELL or CHITOPOLY manufactured by Fuji Spinning Corp. may be effectively used.

Table I provides a list of typical non-woven fabrics for use in the absorbent member of the present invention. Particularly, the spunlaced non-woven fabrics such as listed as No. 3 in Table I are particularly suited for the intended purpose since they exhibit a high elongation rate in a width direction of the channel and also have a high strength.

Exemplified non-woven fabrics suitable for the present invention are illustrated in Table I.

TABLE 1

| No. | Type of N.W. | Raw fiber | Web |
|---|---|---|---|
| 1 | spunbonded | PP × 2.2 d × continuous filament | random |
| 2 | thermally-bonded | PP × 2.2 d × 35 m/m | random |
| 3 | spunlaced | PP × 1.5 d × 45 m/m | parallel |
| 4 | tow | acetate tow | parallel |

| No. | Basis weight (g/m$^2$) | strength (kg/2.3 cm) | | | Elongation (%) | | |
|---|---|---|---|---|---|---|---|
| | | MD | CD | MD/CD | MD | CD | MD/CD |
| 1 | 30 | 5.3 | 2.2 | 2.4 | 30 | 48 | 1.6 |

TABLE 1-continued

| 2 | 32 | 3.9 | 0.6 | 6.5 | 21 | 70  | 3.3  |
|---|----|-----|-----|-----|----|-----|------|
| 3 | 35 | 3.7 | 0.8 | 4.6 | 20 | 230 | 11.5 |
| 4 | 40 | 5.2 | 0.4 | 13  | 15 | 290 | 19.3 |

As described above, the absorbent member of the present invention is constructed by securing the non-woven fabric to at least one face of the highly-stretchable, liquid impermeable elastic sheet continuously in one direction and intermittently in a direction perpendicular to the one direction along the securement portions, forming a plurality of channels extending parallel to each other between the non-woven fabric and the elastic sheet, and positioning the absorbent members in the channels. Accordingly, the absorbent member has excellent elastic and water-proof characteristics. Also the non-woven fabric of the absorbent member provides excellent flexibility and breathability characteristics. Therefore, the present absorbent member is most suitable for use in a variety of articles which contact skin during use, such as disposable diapers, sanitary napkins and the like which are applied to the waist or crotch of the wearer.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. A stretchable absorbent article for fitting about the waist of a wearer, said article comprising:
    a main body comprising an elastic composite sheet,
    said elastic composite sheet comprising an elastic sheet and a non-woven fabric layer secured to at least one surface of said elastic sheet,
    said non-woven fabric layer being secured to said elastic sheet continuously in a first direction and intermittently in a second direction perpendicular to said first direction to define therebetween a plurality of parallel channels extending in said first direction,
    said stretchable absorbent article including juxtaposed dual layers of said elastic composite sheet in the region of at least one of a front waist portion, a rear waist portion, a crotch portion, and portions surrounding leg holes of said main body, each of said elastic composite sheets comprising one of said elastic sheets and one of said non-woven fabric layers.

2. A stretchable absorbent article of claim 1, wherein an absorbent body is mounted inside said main body.

3. A stretchable absorbent article of claim 1, wherein said elastic sheet is a thin-layered sheet selected from a film consisting of a material selected from a natural or synthetic rubber, polyurethane, styrene-butadien block polymer, EVA, LLDPE of ultra low density ethylene-propylene elastomer, ethylene-methylacrylate elastomer and a mixture thereof with a styrene-ethylene-butadien-styrene block copolymer; a co-extruded film of polyurethane elastomers and polyolefine elastomers; and a polyurethane meltblown non-woven fabric.

4. A stretchable absorbent article of claim 1, wherein said non-woven fabric layer comprises hydrophilic synthetic fibers selected from a group consisting of rayon and cotton.

5. A stretchable absorbent article of claim 1, wherein said non-woven fabric layer comprises hydrophobic synthetic fibers selected from a group consisting of polypropylene, polyester, and nylon.

6. A stretchable absorbent article of claim 1, wherein said non-woven fabric layer comprises hydrophobic synthetic fibers treated with surfactants.

7. A stretchable absorbent article of claim 1, wherein said elastic sheet is secured to said non-woven fabric layer in an intermittent pattern.

8. A stretchable absorbent article of claim 2, wherein said absorbent body is arranged to longitudinally extend interior of a crotch portion of the absorbent article, and is secured to an inner surface of a crotch portion at a band-like elongated securement portion thereof positioned centrally transversely thereof.

9. A stretchable absorbent article of claim 2, wherein said absorbent body is arranged to longitudinally extend interior of a crotch portion of the absorbent article, and further extends outwardly of respective transverse sides thereof, said absorbent body being secured to an inner surface of the crotch portion at free ends of the backsheet.

10. An absorbent article having a stretchable region, said stretchable region including a liquid permeable layer, a liquid impermeable elastic layer stretchably secured to said liquid permeable layer at discrete regions to form regions of nonsecurement between adjacent ones of said discrete regions of securement, said liquid permeable layer forming corrugations at the respective regions of nonsecurement for defining respective channels between said liquid permeable layer and said liquid impermeable layer, and absorbent material disposed in selected ones of said channels so that said liquid impermeable plastic layer is stretchable at an area of said selected ones of said channels in a direction generally transverse to said selected ones of said channels.

11. An absorbent article comprising:
    a liquid permeable topsheet;
    a liquid impermeable backsheet having an elastic area, said elastic area being stretchably secured to said liquid permeable topsheet by a plurality of spaced, parallel lines of securement so as to form regions of nonsecurement, said liquid permeable layer respectively forming corrugations at said regions of nonsecurement for defining a plurality of channels between said liquid permeable topsheet and said liquid impermeable backsheet; and
    absorbent material disposed in said channels in a selected location of said absorbent article, said elastic area of said liquid impermeable backsheet being stretchable at said selected location in a direction generally transverse to said channels.

12. An absorbent article of claim 11, wherein said selected location is a crotch region of the absorbent article.

13. An absorbent article of claim 11, wherein said selected location is a lateral central region of the absorbent article.

14. An absorbent article of claim 13, wherein said parallel lines of securement are laterally spaced from each other to define said channels longitudinally extending between front and rear regions of said absorbent article.

15. An absorbent article of claim 14, wherein said absorbent material comprises a plurality of absorbent segments longitudinally arranged in said channel.

16. A stretchable absorbent member, comprising:
a liquid permeable layer;
a liquid impermeable elastic layer stretchably secured to said liquid permeable layer at discrete regions so as to form regions of nonsecurement between said discrete regions of securement, said liquid permeable layer forming corrugations at said respective regions of nonsecurement for defining respective channels between said liquid permeable layer and said liquid impermeable elastic layer; and
absorbent material disposed in selected ones of said channels, said liquid impermeable elastic layer being stretchable at an area of said selected ones of said channels in a direction generally transverse to said channels.

17. A stretchable absorbent member of claim 16, wherein
said absorbent material comprises superabsorbent material.

18. A stretchable absorbent member of claim 16, wherein
said liquid permeable layer comprises a non-woven fabric.

19. A stretchable absorbent member, comprising:
a liquid permeable layer;
a liquid impermeable elastic layer stretchably secured to said liquid permeable layer by a plurality of laterally spaced, parallel lines of securement so as to form regions of nonsecurement, said liquid permeable layer respectively forming corrugations at said regions of nonsecurement for defining a plurality of parallel channels between said liquid permeable layer and said liquid impermeable elastic layer; and
absorbent material disposed in selected ones of said channels, said liquid impermeable elastic layer being stretchable at an area of said selected ones of said channels in a direction generally transverse to said channels.

20. A stretchable absorbent member of claim 19, wherein
said absorbent material has a preshaped configuration having a substantially uniform lateral cross-sectional area.

21. A stretchable absorbent member of claim 20, wherein
said preshaped absorbent material comprises hydrophilic fibers and superabsorbent polymers.

22. A stretchable absorbent member of claim 20, wherein
said preshaped absorbent material comprises a bundle of superabsorbent fibers.

23. A stretchable absorbent member of claim 20, wherein
said lateral cross-sectional area of the preshaped absorbent material is equal to or less than a half of a lateral cross-sectional area of the channel encasing said absorbent material.

24. A stretchable absorbent member of claim 20, wherein
said absorbent member has a plurality of lateral portions, and said channels in one of said lateral portions have a greater lateral cross-sectional area than the channels in an adjacent lateral portion.

25. A stretchable absorbent member of claim 24, wherein
said channels in a central lateral portion of the absorbent structure have a greater lateral cross-sectional area than the channels in lateral portions on opposite sides of said central lateral portion.

26. A stretchable absorbent member of claim 24, wherein
said absorbent material enclosed in the channels in one of said lateral portions have a greater lateral cross-sectional area than the absorbent material in the channels in the adjacent lateral portion.

* * * * *